US006811037B2

(12) United States Patent
Hintsche

(10) Patent No.: US 6,811,037 B2
(45) Date of Patent: Nov. 2, 2004

(54) SENSOR AND/OR SEPARATING ELEMENT AND PROCESS FOR THE PRODUCTION AND USE THEREOF

(75) Inventor: Rainer Hintsche, Berlin (DE)

(73) Assignee: Fraunhofer-Fesellschaft zur Forderung Derangewandten Forschung E.V., Munich (DE)

( * ) Notice: Subject to any disclaimer, the term of this patent is extended or adjusted under 35 U.S.C. 154(b) by 96 days.

(21) Appl. No.: 09/900,924

(22) Filed: Jul. 10, 2001

(65) Prior Publication Data

US 2001/0042711 A1 Nov. 22, 2001

Related U.S. Application Data

(63) Continuation-in-part of application No. 09/214,493, filed on Feb. 19, 1999, now abandoned.

(30) Foreign Application Priority Data

Jul. 11, 1996 (DE) .......................................... 196 28 052

(51) Int. Cl.$^7$ .............................................. B01D 29/46
(52) U.S. Cl. .................. 210/490; 210/500.27; 204/403; 204/409; 204/410; 204/415; 422/50
(58) Field of Search ............................ 210/490, 500.27; 204/403, 409, 410, 415; 422/50

(56) References Cited

U.S. PATENT DOCUMENTS 3,767,552 A 10/1973 Lauer

| | | | |
|---|---|---|---|
| 5,202,011 A | 4/1993 | Kiesele et al. | |
| 5,326,449 A | 7/1994 | Cunningham | |
| 5,985,164 A | 11/1999 | Chu et al. | |
| 6,030,827 A | 2/2000 | Davis et al. | |

FOREIGN PATENT DOCUMENTS

| | | |
|---|---|---|
| DE | 91 11710 | 8/1991 |
| DE | 38 41 621 | 1/1999 |
| DE | 40 18 597 | 1/1999 |
| DE | 41 15 414 | 1/1999 |
| WO | 91 04785 | 4/1991 |

*Primary Examiner*—Ana Fortuna
(74) *Attorney, Agent, or Firm*—Burns, Doane, Swecker & Mathis, L.L.P.

(57) ABSTRACT

The invention provides a mechanically stable substrate having at least one through-opening, a perforated membrane which is integral or fluid-tightly connected with the substrate and which extends across the through-opening, and at least one semi-permeable layer which is applied in firmly adhering manner to one or both sides of the membrane, at least in the perforated region thereof, in that the semi-permeable layer or semi-permeable layers is/are secured mechanically in the adjacent perforations and/or by chemical-structural and/or physical adhesion and/or adhesive intermediate layers and/or covalent surface bonding to the adjacent surfaces of the membrane, optionally of the substrate, or of a metallic film optionally additionally applied to one or both sides of the membrane. The invention further provides a process for the production of this sensor- and/or separating element and the use thereof.

14 Claims, 1 Drawing Sheet

SENSOR AND/OR SEPARATING ELEMENT AND PROCESS FOR THE PRODUCTION AND USE THEREOF

This application is a continuation-in-part of application Ser. No. 09/214,493, filed on Feb. 19, 1999 now abandoned.

DESCRIPTION

The invention relates to a sensor- and/or separating element comprising a membrane arrangement which can be used in particular for the separation of substances and for the detection of molecules in sensor elements as part of separating devices for chemical substances or as part of electrochemical measuring cells and can be used preferentially for chemical analysis in biotechnology and industrial process control.

The invention further relates to a process for the production of the aforesaid sensor- and/or separating element and the use thereof.

As part of an electrochemical measuring cell for the separation of gas molecules and detection in a three-electrode system, DE 3 841 621 C2 has disclosed polymer membranes arranged on support bodies with channels of 50–300 $\mu$m length disposed at a distance from the edge of 5 $\mu$m, said polymer membranes conventionally being polymer membranes used for semi-permeable oxygen diffusion. They are characterised by the fact that the support body consists of metals or plastics with a conductive surface coating. This design is also characterised by an electrolyte which is arranged in the channel structures and together with the metallized or conductive surface forms the three-phase boundary vis-a-vis electrolytic gas.

Similar arrangements comprising a metallic support body as electrode are described in U.S. Pat. No. 3,767,552.

Another device comprising support bodies of the previously mentioned type which form capillaries or capillary-like openings is described in DE 4 018 597 and U.S. Pat. No. 5,202,011. These known arrangements are characterised by solid support structures with relatively long channels between a polymer covering layer and further elements of electrochemical measuring cells. As such solid, voluminous support bodies have a poor molecule-separating capacity, no applications have previously been described for these.

Additionally, DE 41 15 414 C2 has disclosed a sensor- and/or separating element for the semi-permeable diffusion of molecules comprising a mechanically stable substrate having a a through-opening and the semi-permeable membrane arranged in the through-opening. This publication has also disclosed a process for the production of a separating- and/or sensor element wherein a through-opening is formed in a substrate by a processing means, a semi-permeable membrane is introduced into the through-opening and a plurality of electric terminals connected to the membrane are formed.

As here the semi-permeable membrane is formed in the through-openings in that a liquid is introduced therein, from which liquid an ion-selective membrane then forms, relatively thick membranes are obtained which substantially fill the depth of the through-openings very limited. The diffusion capacity is consequently very limited. To improve the diffusion capacity it is necessary to reduce the thickness of the substrate and the cross-sectional area of the through-openings. The possible extent of such a reduction is however dependent upon the particular materials used and therefore such a reduction is possible only to a very limited extent since the stability and durability of the semi-permeable layer and the overall structure are impaired by such a reduction.

Finally, WO 91/11710 A1 has disclosed a sensor- and/or separating element for the semi-permeable diffusion of molecules comprising a mechanically stable substrate having a through-opening and a perforated, semi-permeable membrane connected to the substrate. This document also discloses a process for the production of a sensor- and/or separating element wherein a through-opening is formed in the substrate by a processing means, a semi-permeable membrane is applied to the substrate in such manner that the through-opening is spanned and a plurality of electric terminals are formed.

As in this known sensor- and/or separating element the semi-permeable membrane spans the through-openings, the membrane must be relatively thick if it is to span the relatively large-area through-openings in a stable manner or the cross-sectional area of the through-openings must be relatively small if the membrane is to be made relatively thin. In either case a mutual dependency exists between the nature of the membrane material, the cross-sectional area of the through-openings and the minimum thickness of the membranes with which adequate stability and durability of the membrane across the through-openings are provided. In practice, as in the case of the above described sensor- and/or separating element according to DE 41 15 414 C2, these conditions lead to a relatively low diffusion throughput with relatively limited stability and fairly limited durability of the semipermeable layer.

The object of the present invention is in particular to provide a sensor- and/or separating element of the type mentioned in the introduction which, while providing excellent mechanical stability and durability of the semi-permeable layer, permits a substantially increased diffusion of the molecules to be detected and/or separated.

This object is achieved in accordance with the invention by a sensor and/or separating element for the semi-permeable diffusion of molecules comprising the following:

a) a mechanically stable substrate having at least one through-opening, b) a perforated membrane which is fluid tightly connected to the substrate and which extends at least across the through-openings; and c) at least one semi-permeable layer which is applied in firmly adhering manner to one or both sides of the membrane at least in the perforated region thereof in that the semi-permeable layer or semi-permeable layers is/are secured mechanically in the adjacent perforations and/or by chemical-structural and/or physical adhesion and/or adhesive intermediate layers and/or covalent surface bonding to the adjacent surfaces of the membrane, optionally of the substrate or a metallic film optionally additionally applied to one or both sides of the membrane.

In this way the invention provides a sensor- and/or separating element which permits the throughputs of molecules to be varied and adjusted as desired by means of a practically arbitrary selection of the size and spacing of the perforations of the membrane to which the semi-permeable layer is applied.

Such a sensor- and/or separating element facilitates the provision of a membrane which serves as support membrane for the semi-permeable layer or layers and which is an ultra-thin membrane whose thickness preferably ranges between 50 $\mu$m and 10 nm, particularly preferably between 20 $\mu$m and 100 nm.

Preferably, depending upon its embodiment, the sensor- and/or separating element according to the invention is designed in such manner that A) the semi-permeable layer preferably is a polymer layer, more perferably it consists of one or more organic polymers which is/are preferably adherent or adhesive-like and/or B) the substrate and the membrane are made of similar or different materials from the group consisting of mechanically stable, inorganic and organic materials; and/or C) the substrate and the membrane are made of similar or different organic polymers; and/or D) the organic polymers are from the group consisting of polycarbonate, polystyrene, polytetrafluoroethylene and polyamide; and/or E) the material of the membrane differs from the material of the substrate in respect of its processibility by a predetermined chemical and/or physical processing means, such that the substrate can be removed by the processing means whereas the membrane substantially cannot be attacked by the processing means; and/or F) the membrane preferably consists of silicon, one or more silicon compounds and/or a material containing silicon and/or another semiconductor material, and particularly preferably the membrane consists of silicon dioxide, silicon nitride, silicon oxynitride, glass and/or quartz, while the substrate consists of a material which can be chemically converted into the membrane material or can be coated with the membrane material in firmly adhering manner; and/or G) the perforations have a diameter or maximum diameter which ranges between 0.1 and 50 $\mu$m, preferably 1 and 10 $\mu$m; and/or H) the optional metallic film extends over a region of the substrate or a region of the membrane underlaid by the substrate; and/or I) a metallic film or a plurality of metallic films is/are provided, which consist(s) of individual segments which are separate from one another and each of which is provided with at least one electric terminal; and/or J) a further metallic film or one or more further double layers of metallic film plus semi-permeable layer are applied to the exterior of one or both semi-permeable layer(s), optionally a final metallic film being applied to the outermost semi-permeable layer and all the further metallic films being perforated in the region of the through-opening(s); and/or K) the membrane is electrically non-conductive or semi-conducting and the metallic film on one or both side(s) of the membrane(s) and/or on one or more semi-permeable layer(s) consists of individual segments separate from one another, each of which is provided with at least one electric terminal.

A particularly preferred substrate-membrane material combination is that in which both materials are semiconductor materials, preferably silicon-based materials, such as for example silicon as substrate material and epi-silicon as membrane material.

Another particularly perferred substrate-membrane material combination is that in which both materials are organic polymers, either similar or different organic polymers, e.g., chosen from the group consisting of polycarbonate, polystyrene, polyethylene, polytetrafluoroethylene, polyamide and/or other organic polymers. Such organic polymers can be perforated e.g. by laser radiation, laser ablation, ion beams, preferably followed by etching, or e.g. by mechanical machining as e.g. drilling, milling, embossing, stamping or the like. Such membrane and substrate made of organic polymer can preferably be a thin and a thick foil laminated or adhered together to form the substrate-membrane combination.

In this way, in accordance with the invention, an arrangement comprising one or more semi-permeable layers having the function of molecule-separating membranes, a support element formed as membrane (support membrane) and optionally one or more sensorial metallic films is improved upon in such manner that the support function is now assumed by a mechanically stable membrane integral with the substrate and preferably consisting of inorganic constituents and the semi-permeable layer is connected thereto in firmly adhering manner, thereby facilitating a diffusion improved to a high level with a reduced depth dimension. The metallic film forms a metallic, sensor-like element as used as sensorial component of electrochemical measuring cells and is optionally applied to the interior and/or exterior of the membrane.

In accordance with the invention, in place of the previously conventional voluminous lattice-, capillary or sieve/filter constructions, a preferably ultra-thin mechanical membrane is used. Here it is possible to use a technological process as conventionally employed in silicon technology and micromechanics with which, for example by the etching of silicon, glass or the like, pits, holes or the like can be produced as through-openings in silicon, glass and other materials, where at the end of such a through-opening an ultra-thin layer of membrane-forming organic materials, such as silicon dioxide, silicon nitride, silicon oxynitride or epi-silicon remains as membrane and thus the material of said membrane is selected such that it is not attacked by the etching agent or the like of the substrate. The thickness of such membranes is determined and adjusted by the preceding application of the materials to the substrate, which consists for example of silicon, glass or the like.

For example by means of a photolithographic process using wet-chemical or dry-etching procedures it is possible to introduce pores and openings of any desired size as perforations into the membrane so that an adjustable permeability is achieved via the size and number of these openings.

These perforations and their permeability are of particular advantage for adjusting the diffusion or penetration of molecules or atoms through the supporting membrane.

For the provision of a sensorial element, such as an electrode, or in order to change the chemical surface structure, preferably ultra-thin metallic films are applied, for example in accordance with the known technological principle of sputtering or thermal vapour deposition, to the upper side or rear side of the support membrane onto the pit-like through-openings. These metallic films can be provided externally or internally with an electric connection line to enable them to be used for example as electro-chemically operating electrodes. Due to the preferably planar arrangement, the metallic films can be structured in a simple manner, for example by mask technology, and then used as multi-channel electrodes.

The mechanical structuring of the membrane, which supports the semi-permeable layer(s), with perforations has a particularly advantageous effect in that these serve as mechanical fixing means for the semi-permeable layer(s), perferably produced from plastics material, which is/are optionally applied to one or both sides of the membrane. To strengthen the adhesion, known surface modifications can be provided, such as silanisation or chemical bonding with bifunctional reagents following the functionalisation of the surface.

The arrangement of semi-permeable layers, such as polymer membranes, on ultra-thin support membranes has the advantage that these can be designed for high diffusion rates of molecules, such as for example those af gases, and for this reason they can also fulfil separating functions, for example in gases.

The metallic films can be used as an electrochemical sensor element in cooperation with the semi-permeable layers, such as for example polymer membranes, and used for example as electrodes in electrochemical cells, it being possible to use conventional electrolytes and additional electrodes on one side of the sensor- and/or separating element.

The invention also provides a process for the production of the sensor- and/or separating element according to the invention which is in no way limited to the particularly preferred embodiments of specific process steps referred to in the foregoing only by way of example, but rather generally comprises the following detailed process steps:

(a) providing a mechanically stable substrate;
(b) forming at least one through-opening in the substrate;
(c) fluid-tightly connecting a membrane to the substrate such that the membrane extends at least across the through-opening;
(d) forming perforations through the membrane in the region of the through-opening(s);
(e) applying at least one semi-permeable layer in firmly adhering manner to one or both sides of the membrane at least in the region thereof spanning the through-opening(s), preferably also to the adjacent region of the substrate, in that the semipermeable layer or semi-permeable layers is/are secured mechanically in the adjacent perforations and/or by chemical-structural and/or physical adhesion and/or adhesive intermediate layers and/or covalent surface bonding to the adjacent surfaces of the membrane and optionally of the substrate.

This process can preferably be realized in detail by:

(1) applying a metallic film on one or both sides of the membrane and forming one or more electrical terminals connected to or formed by the membrane(s); and/or
(2) with the substrate and the membrane being made of similar or different materials from the group consisting of mechanically stable, inorganic and organic materials; and/or
(3) the substrate and the membrane being made of similar or different organic polymers;
(4) prefably in the latter case the organic polymers being from the group consisting of polycarbonate, polystyrene, polytetrafluoroethylene and polyamide.

Another process provided by the invention comprises the following detailed process steps:

a) provision of an electrically insulating or semiconducting membrane on a mechanically stable substrate such that the membrane is integral with the substrate, where the material of the membrane differs from the material of the substrate in respect of its processibility by a predetermined chemical and/or physical processing means, such that the substrate can be removed by this processing means whereas the membrane substantially cannot be attacked by the same processing means;
b) formation of at least one through-opening in the substrate by the processing means so that the through-opening is closed off on one side by the membrane;
c) formation of perforations in the region of the membrane extending across the through-opening;
d) application of at least one semi-permeable layer in firmly adhering manner to one or both sides of the membrane at least in the region thereof spanning the through-opening(s), preferably also to the adjacent region of the substrate in that the semi-permeable layer or semi-permeable layers is/are secured mechanically in the adjacent perforations and/or by chemical-structural and/or physical adhesion and/or adhesive intermediate layers and/or covalent surface bonding to the adjacent surfaces of the membrane and optionally of the substrate or of a metallic film optionally additionally applied to one or both sides of the membrane.

If, as is possible within the scope of the invention, an electrically conductive membrane is used instead of an electrically insulating or semiconducting membrane, the process according to the invention can also be executed in the above manner, it being possible to use the electrically conductive membrane as metallic film which can be provided with one or more electrically conductive terminals.

In accordance with a further development of the above processes according to the invenion, sensor- and/or separating elements of elaborate structures can be produced in that a further metallic film or one or more double layers of metallic film plus semi-permeable membrane(s) are applied to the exterior of one or both semi-permeable layers, where optionally a final metallic film is applied to the outermost semi-permeable membrane and where all the further metallic films are perforated in the region of the through-opening(s) and where the further metallic film or one or more or all of the further metallic films can be formed in the segmented manner described in the following.

Preferred embodiments of the above process according to the invention are additionally characterised in that:

1) a metallic film or a plurality of metallic films is/are produced from segments separate from one another, each segment preferably being provided with or electrically conductively connected to at least one separate terminal and/or
2) the perforations are formed with a diameter or maximum diameter ranging between 0.1 and 50 $\mu$m, preferably 1 and 10 $\mu$m and/or
3) the semi-permeable layer(s) is/are applied by a spin-off process, centrifugal or fluidized-bed coating, or spin-or jet coating and/or
4) mechanical machining, laser ablation, chemical wet etching, plasma dry-etching, electro-erosion or thermal melting-out is used as means of forming the through-opening(s) and/or
5) all or a part of the perforations are formed by photolithography in association with dry- or wet etching or by laser beam processing or by ion beam processing and/or
6) the metallic film or all the metallic films or a part of the metallic films is/are applied by sputtering, vapour deposition, plating, electrolytic deposition or current-free electrolytic deposition.

Further preferred features of the invention are described in the claims.

The sensor- and/or separating element according to the invention and/or produced by the process according to the invention can be used in particular for the detection of electro-chemically active molecules and for the separation of molecules through the semi-permeable layer(s).

The advantage of the invention consists in particular in that the preferably ultra-thin membrane results in improved material transport properties and improved fixing of the semi-permeable layer(s), for example in the form of polymer membranes, on the supporting membrane. A further advantage consists in the preferably very cheap production using conventional semiconductor technology or plastics technology processes and in the very easily variable arrangement and dimensioning of the perforations in the membrane (support membrane). Compared with the previously conventionally used processes in LIGA technology or bulk micro-machining with voluminous support elements, exceptional advantages are obtained in terms of economy and handling.

The above described, and further, advantages and features of the invention will be explained in the following in the form of a few particularly preferred embodiments of the sensor- and/or separating element according to the invention making reference to the drawings in which.

Figure 2:
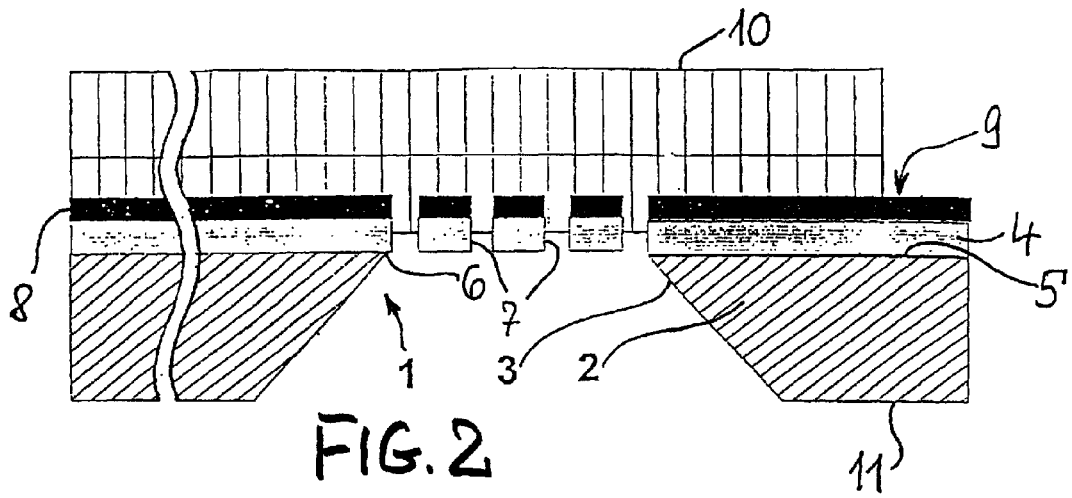
FIG. 2 is a section along the line X-X' through the sensor- and/or separating element according to FIG. 1
Figure 1:
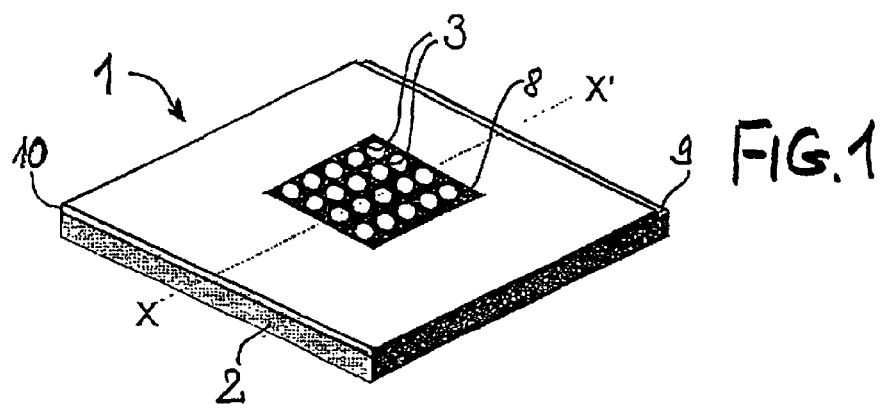
FIG. 1 is a perspective view of a first embodiment of a sensor- and/or separating element according to the invention.

Reference will firstly be made to FIGS. 1 and 2 in which the sensor- and/or separating element, bearing the overall reference 1 and suitable for the semi-permeable diffusion of molecules, comprises the following:

1) A mechanically stable substrate 2 which in the present case consists of silicon wafer and is provided with through-openings 3 which in the case of etching out said through-openings are conical or more generally "pit-shaped", 20 such through-openings 3 forming a regular arrangement in the present example as shown in FIG. 1.

2) A membrane 4 which is integral with the substrate and which in the present example consists of epi-silicon and has a thickness ranging between 100 nm and 50 μm. This membrane 4 extends across the through-opening 3 and in the present case across all of the upper side 5 of the substrate 2, although it is also possible for the membrane to extend only across the region of the through-opening 5 adjacent to the edge 6, for example but not necessarily when only one single through-opening is provided. It is important that the membrane 4 is integral with the substrate so that it is supported and held by the substrate in a firmly adhering manner. In the region of the through-opening 3 adjacent to the membrane 4, the membrane is provided with perforations 7 which in the present case are circular and have a diameter ranging between 1 and 10 μm, which perforations have not been illustrated in FIG. 1. In this connection it should be noted that the Figures of the drawing are not necessarily true to scale, the emphasis having been placed on illustrating the principles of the present invention.

3) A metallic film 8 which is arranged on the upper side of the membrane 4, i.e. the side of the membrane which faces away from the substrate 2 and whose thickness in the present case ranges between 0.1 and 50 μm. This metallic film 8 is provided with an electric terminal 9, in the present case in the form of a terminal surface freely accessible from the exterior.

4) A semi-permeable layer 10 which is applied to the metallic film and, as illustrated in FIG. 2, extends in part into the perforations 7 through the membrane 4 and the metallic film 8, thus ensuring a good, firmly adhering fixing of the semi-permeable layer 10, preferably composed of polymer material, to the remaining structure of the sensor- and/or separating element 1. This semi-permeable layer 10 forms a separating membrane for the diffusion-separation of separating molecules.

Figure 3:
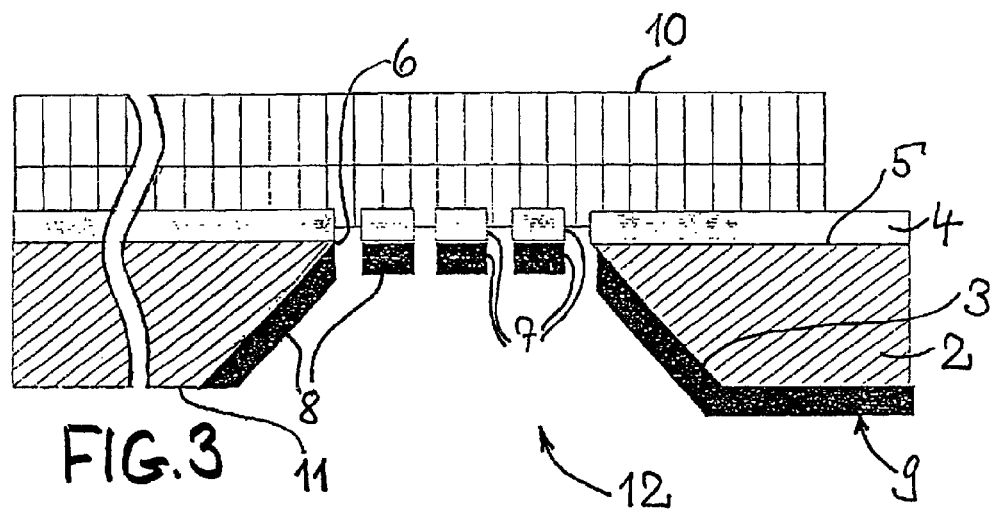
FIG. 3 is a section corresponding to FIG. 2 through a second embodiment of a sensor- and/or separating element according to the invention.

The embodiment according to FIG. 3 differs from the embodiment according to FIGS. 1 and 2 in that the metallic film 8 is applied to the side of the membrane 4 facing towards the substrate 2 and to the wall surface of the through-openings 3 and of the exposed underside 11 of the substrate 11. Consequently the same references have been used in FIG. 3 as in FIGS. 1 and 2 with the exception of the reference numeral 12 which designates the entire sensor- and/or separating element.

A preferred embodiment of the process for the production of the sensor- and/or separating element 1 according to FIGS. 1 and 2 comprises in particular the following process steps:

a) Provision of a thin, preferably ultra-thin, membrane 4 on the solid substrate 2, i.e. the substrate not yet provided with the through-openings 3, such that the membrane 4 is integral with the substrate 2, where the material of the substrate 2 in the present case is silicon while the material of the membrane 4 is epi-silicon so that consequently the two materials possess chemically different etchability (this material combination merely being one example of a plurality of silicon-based materials in semiconductor technology).

b) Chemical wet-etching of the substrate 2 using a lithographic mask applied to the underside 11 of the substrate 2 so that the silicon of the silicon wafer provided as substrate 2 is removed in the region of the through-opening 3 while the material of the membrane 4 substantially is not attacked by the etching liquid used for the chemical wet-etching of the silicon and remains so that the membrane 4 closes off the through-opening 3 on one side in this process step.

c) Formation of the perforations 7 in the membrane 4 in that, using a photolithographic process, the membrane 4 is covered outside of the regions provided for the perforations 7 and the perforations 7 are etched through the membrane by means of a plasma dry-etching process so that the perforations 7 form a network-like structure of openings, namely perforations.

d) Application of the metallic film 8, for example by sputtering or vapour deposition, to the side of the membrane 4 facing away from the substrate 2.

e) Application of the semi-permeable layer 10, in the present case consisting of polymer material, in firmly adhering manner to the exposed side of the metallic film 8, for example by a centrifugal procedure using a spin-off process.

f) Formation of an electric terminal 9 by removal of the material of the semi-permeable layer 10 in a suitable region, in the present case in the edge region, so that the metallic film 8 can be connected to an electric line by suitable contacting means not shown here.

The process for the production of the sensor- and/or separating element 12 according to FIG. 3 differs from the process d) described above only in that the metallic film 8 is applied to the membrane 4 provided with the perforations 7 in accordance with process step d) from the exposed side of the through-opening 3 so that the wall of the through-opening and at least a part of the adjacent underside 11 of the substrate 2 are simultaneously provided with the metallic film 8 and the electric terminal 9 is thus also formed. In the case of this procedure the semi-permeable layer 10 is applied directly to the membrane 4.

In particular the invention comprises the following structures of a sensor- and/or separating element as an arrangement of semi-permeable layers (sensor membranes) for the diffusion of molecules (also to include atoms), in particular on sensorial elements (metallic films):

i) An arrangement wherein a metallic film as sensorial element and a semi-permeable, preferably polymeric separating layer are arranged on an ultra-thin, perforated, mechanical support membrane.

ii) An arrangement wherein the support membrane consists of mechanically stable, membrane-forming inorganic materials such as $SiO_2$, $SiN_x$, epi-silicon or others and its thickness ranges particularly preferably between 100 nm and 20 $\mu$m, although it can also be thinner and thicker.

iii) An arrangement wherein the support membrane is provided with perforations whose size amounts particularly preferably to approximately 1–10 $\mu$m and whose geometric shape and distribution can be selected variably and which can be adapted to the combination and properties of additional layers.

iv) An arrangement wherein the support membrane forms the base of one or more pits in a mechanically stable material, such as for example silicon or glass.

v) An arrangement wherein at least one conductive metallic film, preferably composed of noble metals, is applied as sensitive element in accordance with the electrode principle to both sides or optionally one side of the support membrane and in each case has an electric connection line, but can also consist of structured segments with a plurality of connection lines.

vi) An arrangement wherein a semi-permeable, preferably organic polymer membrane, preferably an adherent polymer membrane, is applied to the support membrane with or without the metallic film, which polymer membrane is secured in stable manner by chemical adhesion and/or covalent surface bonding and/or mechanical fixing in the openings of the support membrane.

vii) An arrangement which advantageously can be used to detect electrochemically active molecules as part of an electrochemical cell.

viii) An arrangement which can be used extremely favourably for the semi-permeable separation of molecules and transport into the space situated behind the semi-permeable layer or semi-permeable layers.

The above described embodiments of the sensor- and/or separating element according to FIGS. 1 to 3 and of the method for its production can preferably be modified in the following manner:

(A) The substrate 2 and the membrane 4 can be made of plastics, preferably organic polymers, either of similar or identical organic polymers or of different organic polymers, e.g., of polycarbonate, polystyrene, polyethylene, polytetrafluoroethylene, polyamide or others.

(B) The membrane 4 of organic polymer can be a foil or sheet laminated on or adhered to a substrate 2 of organic polymer, which latter can be a thicker foil or sheet.

(C) The perforations in the membrane and/or the through-openings in the substrate can be obtained e.g. by laser ablation, ion beam processing (preferably followed by etching) and/or by machining as e.g. by drilling, milling, embossing, stamping, grinding or the like.

Thus, in this case the above method steps a) to c) are replaced by providing a thin membrane of plastics, referably organic polymer, on a thicker substrate of plastics, preferably, organic polymer, in fluid-tight manner, with providing the substrate with through-openings, preferably before the connection with the membrane, and providing the membrane with perforations, preferably after the connection with the substrate. The other steps and all dimensions can be the same as above.

What is claimed is:

1. A sensor- and/or separating element for the semi-permeable diffusion of molecules comprising:

a) a mechanically stable substrate having at least one through-opening, b) a perforated membrane which is fluid-tighly connected to the substrate and extends at least across the through-opening; and c) at least one semi-permeable layer which is applied in firmly adhering manner to one or both sides of the membrane at least in the perforated region thereof, wherein the semi-permeable layer or semi-permeable layers is/are secured mechanically in the adjacent perforations and/or by chemical-structural and/or physical adhesion and/or adhesive intermediate layers and/or covalent surface bonding to the adjacent surfaces of the membrane, optionally of the substrate, or of a metallic film optionally additionally applied to one or both sides of the membrane.

2. A sensor- and/or separating element according to claim 1, wherein the substrate and the membrane are made of similar or different materials from the group consisting of mechanically stable, inorganic and organic materials.

3. A sensor- and/or separating element according to claim 2, wherein the substrate and the membrane are made of similar or different organic polymers.

4. A sensor- and/or separating element according to claim 3, wherein the organic polymers are from the group consisting of polycarbonate, polystyrene, polytetrafluoroethylene and polyamide.

5. A sensor- and/or separating element according to claim 2, wherein the material of the membrane differs from the material of the substrate in respect of its processibility by a predetermined chemical and/or physical processing means, such that the substrate can be removed by the processing means whereas the membrane substantially cannot be attacked by the processing means.

6. A sensor- and/or separating element according to claim 5, wherein the materials of the substrate and the membrane are chosen from the group consisting of silicon, one or more silicon compounds and/or a material containing silicon and/or another semiconductor material.

7. A sensor- and/or separating element according to claim 6, wherein the substrate is of silicon and the membrane is of epi-silicon.

8. A sensor- and/or separating element according to claim 1, characterized in that the membrane is an ultra-thin membrane whose thickness ranges between 20 $\mu$m and 100 nm.

9. A sensor- and/or separating element according to claim 1, characterized in that the semi-permeable layer is a polymer layer, preferably composed of an organic, preferably adherent, polymer.

10. A sensor- and/or separating element according to claim 1, characterized in that the perforated membrane has perforation having a diameter or maximum diameter which ranges between 0.1 and 50 $\mu$m.

11. A sensor- and/or separating element according to claim 1, characterized in that the optional metallic film extends over a region of the substrate or over a region of the membrane underlaid by the substrate.

12. A sensor- and/or separating element according to claim 11, characterized in that a further metallic film or one or more further double layer(s) of metallic film plus semi-permeable layer are applied to the exterior of one or both of the semi-permeable layers, where optionally a final metallic film is applied to the outermost semi-permeable layer and where all the further metallic films are perforated in the region of the through-opening.

13. A sensor- and/or separating element according to claim 1, characterized in that a metallic film or a plurality of metallic films is/are provided, which consist(s) of individual segments which are separate from one another and each of which is provided with at least one electric terminal.

14. A sensor- and/or separating element according to claim 1, characterized in that the perforated membrane has perforations having a diameter or maximum diameter which ranges between 1 and 10 $\mu$m.

* * * * *

UNITED STATES PATENT AND TRADEMARK OFFICE
CERTIFICATE OF CORRECTION

PATENT NO. : 6,811,037 B2
DATED : November 2, 2004
INVENTOR(S) : Rainer Hintsche It is certified that error appears in the above-identified patent and that said Letters Patent is hereby corrected as shown below:

<u>Title page,</u>
Item [73], Assignee, change "Fraunhofer-Fesellschaft zur Forderung Derangewandten Forschung E.V." to -- Fraunhofer-Gesellschaft zur Förderung der angewandten Forschung E.V. --

Signed and Sealed this

Twenty-ninth Day of March, 2005

JON W. DUDAS
*Director of the United States Patent and Trademark Office*